US00RE35616E

United States Patent [19]

Tillotson et al.

[11] E Patent Number: Re. 35,616

[45] Reissued Date of Patent: Sep. 30, 1997

[54] ELASTOMERIC COVERING MATERIAL AND HAND GLOVE MADE THEREWITH

[75] Inventors: Neil E. Tillotson, Dixville Notch, N.H.; Luc G. DeBecker, Vancleave, Miss.

[73] Assignee: Tillotson Corporation, Boston, Mass.

[21] Appl. No.: 556,080

[22] Filed: Nov. 13, 1995

Related U.S. Patent Documents

Reissue of:

[64] Patent No.: 5,014,362
Issued: May 14, 1991
Appl. No.: 522,390
Filed: May 11, 1990

[51] Int. Cl.[6] ..... A41D 19/00

[52] U.S. Cl. ..... 2/168; 2/167

[58] Field of Search ..... 2/168, 161.7, 167, 2/169, 161.6, 159, 163, 164; 524/430, 432, 433, 434, 436; 526/338

[56] References Cited

U.S. PATENT DOCUMENTS

| | | | |
|---|---|---|---|
| 2,577,345 | 12/1951 | McEwen | 128/294 |
| 2,880,189 | 3/1959 | Miller | 260/29.7 |
| 3,759,254 | 9/1973 | Clark | 128/79 |
| 4,096,135 | 6/1978 | Ohishi et al. | 260/79.5 B |
| 4,115,873 | 9/1978 | Stansbury | 2/163 |
| 4,508,867 | 4/1985 | Sato | 524/434 |
| 4,590,123 | 5/1986 | Hashimoto et al. | 428/316.6 |
| 4,684,490 | 8/1987 | Taller et al. | 264/296 |
| 4,834,114 | 5/1989 | Boarman | 128/830 |
| 4,855,169 | 8/1989 | McGlothlin et al. | 428/35.2 |
| 4,945,923 | 8/1990 | Evans et al. | 128/842 |
| 4,963,623 | 10/1990 | Miller et al. | 525/604 |
| 4,971,071 | 11/1990 | Johnson | 128/842 |

FOREIGN PATENT DOCUMENTS 59-124831 7/1984 Japan .

*Primary Examiner*—Amy B. Vanatta
*Attorney, Agent, or Firm*—Jones & Askew

[57] ABSTRACT

An elastomeric material and gloves made therewith are substantially impermeable to water vapor and liquid water, have a relatively high tensile strength, and have a relatively low resilience. The gloves conform to the shape of a hand when stretched to fit about the hand and then relax so that the pressure exerted on the hand is substantially reduced. The gloves are particularly useful in medical applications and most particularly useful as surgical gloves.

21 Claims, 1 Drawing Sheet

ELASTOMERIC COVERING MATERIAL AND HAND GLOVE MADE THEREWITH

Matter enclosed in heavy brackets [ ] appears in the original patent but forms no part of this reissue specification; matter printed in italics indicates the additions made by reissue.

TECHNICAL FIELD

The present invention generally relates to elastomeric materials, and more particularly relates to flexible latex gloves useful in medical applications.

BACKGROUND OF THE INVENTION

Coverings made with elastomeric materials are well known and find many useful applications. One such application is known as the "latex glove." Latex gloves are made from a variety of elastomers and during the glove-making process the elastomers are normally in their latex form. Latex gloves are often desirable because they can be made light, thin, flexible, tightly-fitting and substantially impermeable to some liquids and gases such as liquid water and water vapor.

The characteristics of latex make latex gloves useful in medical applications, and particularly useful as surgical gloves. Surgeons are required to perform delicate operations with their hands while wearing latex gloves. Surgical operations often last for hours. To maintain accurate control over instruments with their hands, surgeons must wear relatively thin latex gloves which fit closely to their skin so that they can grip and feel the instruments in their hand almost as if they were not wearing gloves at all. Thus, conventional latex surgical gloves are thin and undersized so as to fit tightly onto the surgeons' hands. However, conventional latex surgical gloves, which are often made of natural rubber, are very resilient and, when stretched to fit about the wearer's hand, apply pressure to the wearer's hand. With conventional latex surgical gloves, this pressure is not appreciably released until the wearer removes the gloves. The pressure applied by conventional latex surgical gloves restricts the blood vessels in the hands of the wearer and restricts the movement of the wearer's fingers. Thus, when worn for an extended period of time, the pressure applied by conventional latex surgical gloves tends to numb and fatigue the wearer's hands and causes general discomfort for the wearer. During a long surgical operation, this can cause surgeons some difficulty in controlling instruments with their hands.

Accordingly, there is a need for an elastomeric material which is suitable as a covering, but which relaxes after being stretched about an object. More particularly, there is a need for a latex surgical glove that, when stretched to fit the wearer's hand, conforms to fit closely about the wearer's hand and then relaxes to relieve the pressure applied by the glove to the wearer's hands and give the wearer greater comfort and greater sensitivity in performing delicate tasks.

SUMMARY OF THE INVENTION

Accordingly, an object of the present invention is to provide an improved latex glove.

Another object of the present invention is to provide a latex glove which does not numb or fatigue the hand of the wearer when worn for an extended period of time.

Another object of the present invention is to provide a latex glove which conforms to the wearer's hand, but does not exert pressure on the wearer's hand for an extended period of time.

A further object of the present invention is to provide an elastomeric material useful in forming a covering or glove than when stretched to cover an object conforms to the shape of the object and then relaxes to reduce the pressure exerted upon the object.

This invention fulfills these and other objects by providing an elastomeric material characterized by being substantially impermeable to water vapor and liquid water, having a relatively high tensile strength, and having a relatively low level of resilience. More specifically, the elastomeric material of the present invention is characterized by having a tensile strength of at least about 1500 psi as measured according to ASTM D-412 on a sample of the elastomeric material having a thickness from about 4.0 to about 4.5 mils, and having elastic properties such that when the elastomeric material is stretched from an initial configuration to fit about an object, the elastomeric material conforms to the configuration of the object, initially exerting a predetermined pressure on the object and thereafter relaxing to exert on the object a reduced pressure which is substantially less than about 80% of the predetermined pressure.

Preferably, the material of the present invention comprises nitrile butadiene rubber and a metallic compound which is substantially insoluble in water and is present in the amount effective to impart sufficient tensile strength without significantly stiffening the elastomeric material and altering the elastomeric properties. More preferably, the material of the present invention comprises carboxylated nitrile butadiene rubber.

The metallic compound preferably comprises a metal selected from the group consisting of lead, magnesium and zinc. More preferably, the metallic compound is a metallic oxide. Preferred metallic oxides include lead oxide, magnesium oxide and zinc oxide. Zinc oxide is the most preferred metallic compound. Zinc oxide is preferably present in the material in an amount from about 0.1 to about 0.5 parts per 100 parts nitrile butadiene rubber.

According to another aspect, the present invention comprehends a glove comprising a layer of the elastomeric material of the present invention. The glove of the present invention has an initial configuration adapted to receive a hand. Because the glove of the present invention comprises a layer of the elastomeric material of the present invention, the glove of the present invention has elastic properties such that when stretched from the initial configuration to fit about a hand, the glove conforms to the configuration of the hand initially exerting a predetermined pressure on the hand and thereafter relaxing to exert on the hand a reduced pressure which is substantially less than about 80% of the predetermined pressure. In addition, the glove of the present invention has a relatively high tensile strength and is substantially impermeable to water vapor and liquid water. Accordingly, the glove of the present invention is particularly useful as a surgical glove. After being donned by the wearer, the glove of the present invention relaxes so that the pressure on the wearer's hand is substantially reduced, but remains closely fitted about the wearer's hand. Thus, the glove of the present invention may be worn for an extended period of time without diminishing the sensitivity of the wearer's hand or becoming uncomfortable.

Other features, objects, and advantages of the present invention will become apparent from the following detailed description, drawings, and claims.

DETAILED DESCRIPTION

Figure 1:
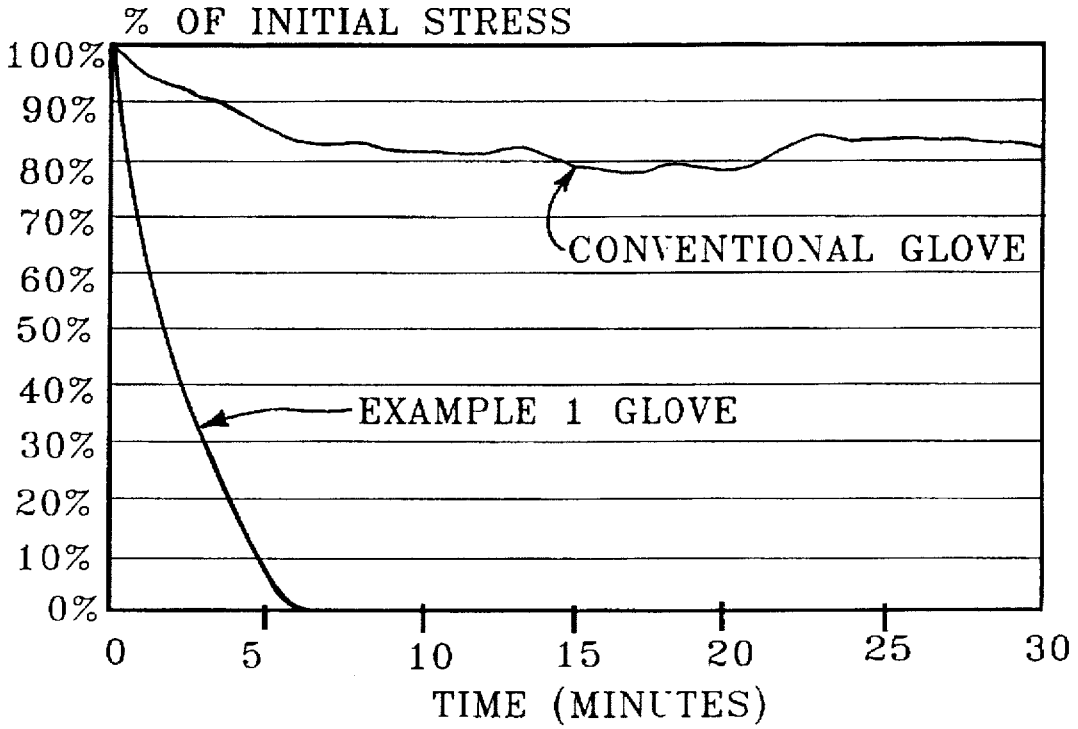
FIG. 1 is a graph comparing the percent of initial stress required to maintain the stretch of a latex glove made according to a preferred embodiment of the present invention to that required by a conventional latex glove.

Generally described, the elastomeric material of the present invention is characterized by being substantially impermeable to water vapor and liquid water, having a relatively high tensile strength, and having a relatively low resilience. These properties make the elastomeric material of the present invention particularly useful as a covering, and even more particularly useful as a glove.

The elastomeric material of the present invention has the following properties as measured according to ASTM D-412 on a sample having a thickness from about 4.0 to about 4.5 mils: a tensile strength greater than about 1500 psi and preferably greater than about 2000 psi, and a elongation greater than about 700% and preferably greater than about 800%, and a 500% modulus less than about 350 psi and preferably between about 250 and about 300 psi. The tensile strength is the energy required to stretch the sample to the breaking point and the elongation is the percent stretch of the sample at the breaking point. The 500% modulus is a measure of the energy it takes to stretch the sample 500% of a predetermined length. The elastomeric material of the present invention and gloves made therewith also have a high level of puncture resistance. The elastomeric material of the present invention has a puncture resistance as measured according to ASTM D-120 on a sample having a thickness between 4.0 and 4.5 mils of greater than about 800 pounds per inch.

The high level of strength as illustrated by the foregoing properties, enables the elastomeric material of the present invention and gloves made therewith to be pulled and stretched a considerable amount before breaking. Thus, a glove made with the elastomeric material of the present invention can be made to fit closely to the wearer's skin because it can be pulled with a considerable amount of force when being donned by the wearer. This is particularly important for surgical gloves which must be thin and fit closely.

The relatively low resilience, allows the elastomeric material of the present invention and gloves made therewith to relax after being stretched while the stretch is maintained. In other words, the elastomeric material of the present invention has elastic properties such than when the elastomeric material is stretched from an initial configuration to fit about an object such as a hand, the elastomeric material conforms to the configuration or the object, initially exerting a predetermined pressure on the object and thereafter relaxing to exert on the object a reduced pressure which is substantially less than about 80% or the predetermined pressure. Preferably, the elastomeric material of the present invention and gloves made therewith are further characterized by having elastic properties such that the significantly reduced pressure is reached within six minutes after the material is stretched to fit about the object or hand. More preferably, the elastomeric material of the present invention and gloves made therewith are further characterized by having elastomeric properties such that the reduced pressure becomes less than about 50% of said predetermined pressure within about one minute after the material is stretched to fit about the object or hand. Most preferably, the elastomeric material of the present invention and gloves made therewith are further characterized by having elastomeric properties such that the reduced pressure becomes less than [bout 90%] *about 10%* of said predetermined pressure within about six minutes after the material is stretched to fit about the object or hand.

Figure 2:
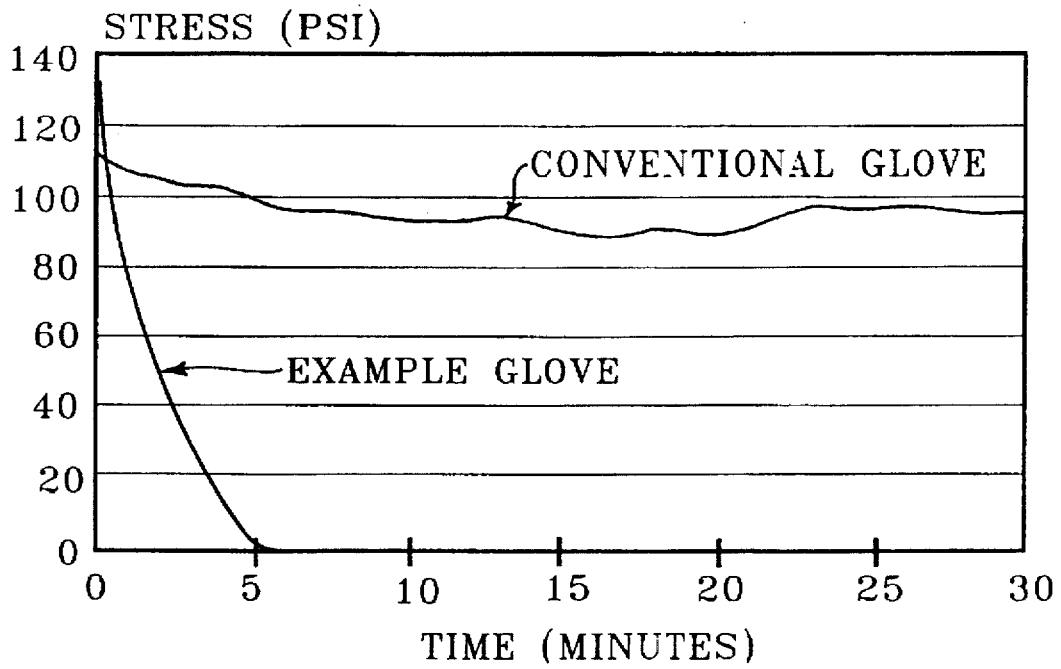
FIG. 2 is a graph comparing the stress required to maintain the stretch of a latex glove mile according to a preferred embodiment of the present invention to that required by a conventional latex glove.

Accordingly, gloves made with the elastomeric material of the present invention are particularly useful as surgical gloves because they relax on the hands of the wearer after being donned so that there is little resistance to movement by the wearer's fingers and there is little restriction of blood vessels in the wearer's hands. Thus, gloves made with the elastomeric material of the present invention can be worn for extended periods of time without tiring or numbing the hands of the wearer, thereby giving the wearer greater comfort and greater sensitivity in performing delicate tasks. The elastic properties of the gloves of the present invention are illustrated in FIGS. 1 and 2 discussed hereinbelow.

Preferably, the elastomeric material of the present invention comprises nitrile butadiene rubber and a metallic compound which is substantially insoluble in water and is present in an amount effective to impart sufficient tensile strength to the elastomeric material without significantly stiffening elastomeric material and altering the elastic properties of the elastomeric material. The nitrile butadiene rubber is preferably carboxylated nitrile butadiene rubber which when cured possesses a higher tensile strength than noncarboxylated nitrile butadiene rubber.

The metallic compound preferably comprises lead, magnesium or zinc. Representative compounds are metallic oxides, such as lead oxide, magnesium oxide or zinc oxide. Zinc oxide is preferred. In addition, zinc oxide is preferably present in the elastomeric material in an amount from about 0.1 to about 0.5 parts per hundred parts nitrile butadiene rubber. If the zinc oxide is not present or is present in an amount below this range, the tensile strength of the elastomeric material is reduced and gloves made therewith tear easily. If the zinc oxide is present in an amount above this range, the elastomeric material and gloves made therewith become more stiff and their resilience is reduced. At the higher resilience, gloves made with the elastomeric material maintain undesirable pressure on the hands of the wearer.

The gloves of the present invention are preferably made by dipping a glove form into a latex mixture, curing the latex mixture on the glove form at elevated temperatures, and then stripping the cured latex glove from the glove form. The resulting gloves preferably have a thickness from about 4.0 to about 4.5 mils.

The latex mixture preferably comprises carboxylated nitrile butadiene rubber latex having about a 40% dry rubber content and zinc oxide in the amount from about 0.1 to about 0.5 parts per hundred parts rubber. The latex mixture may also include additives commonly used to make cured latex products such as processing agents, pH control agents, accelerating agents, curing agents, coagulants, and colorants. As will be appreciated by those skilled in the art, the amounts of these additives may be varied considerably. This preferred latex mixture is preferably cured in an oven for 30 to 40 minutes at 270 to 300 degrees Fahrenheit.

The present invention is further illustrated by the following example which is designed to teach those of ordinary skill in the art how to practice this invention and represent the best mode contemplated for carrying out this invention.

EXAMPLE 1

Latex gloves were made as follows. A latex material having the formula set forth in Table 1 was thoroughly mixed in a container. The amount of each component of the material is set forth in parts per hundred dry rubber (PHR). Table I shows the amount of dry carboxylated nitrile butadiene rubber present in the latex composition; however, the carboxylated nitrile butadiene rubber was added to the latex composition as a latex comprising 40% by weight of carboxylated nitrile butadiene rubber with the remainder water and surfactants. The sodium dodecylbenzene sulfonate is a processing agent, the potassium hydroxide is present as a pH control agent, the sulfur is a curing agent, the zinc dibutyl dithiocarbamate is an accelerating agent, the titanium dioxide is present as a pigment, the MICHEMLUBE 135 is a paraffin wax emulsion available from Michelman, Inc., Cincinnati, Ohio, and the COAGULANT WS is a polyether-polysiloxane coagulant available from Bayer, Inc.

Glove forms were prepared by washing with a detergent and rinsing. The glove forms were then dipped in a coagulant mixture comprising calcium nitrate, water and a nonionic soap to promote congealing of the latex around the glove forms. After being dipped in the coagulant mixture, the glove forms were dipped in the latex material. The latex coated glove forms were then dipped in a leach consisting of warm water and then into a powder slurry consisting of powdered starch. The latex coated glove forms were then placed in an oven for 30 minutes at 285 degrees Fahrenheit to cure the latex. After removal from the oven, the cured latex coated glove forms were dipped in a post curing leach consisting of warm water. The cured latex gloves were then stripped from the glove forms and tumbled.

TABLE 1

EXAMPLE 1 LATEX FORMULATION

| | PHR |
|---|---|
| Carboxylated nitrile butadiene rubber (dry) | 100.0 |
| Sodium dodecylbenzene sulfonate | 0.25 |
| Potassium hydoxide | 0.7 |
| Sulfur | 1.0 |
| Zinc didutyl dithiocarbamate | 1.0 |
| Zinc oxide | 0.5 |
| Titanium dioxide | 4.0 |
| MICHELMLUBE 135 | 3.0 |
| COAGULANT WS | 2.0 |
| STAN-TONE WD 2467 pigment | 0.1 |
| CHERRY FLAVOR #50767 pigment | 0.7 |

The gloves from Example 1 were subjected to a series of tests, the results of which are shown in Tables 2 and 3 and FIGS. 1 and 2. The tensile strength, elongation, and 500% modulus of the gloves made according to Example 1 were each measured according to ASTM D-412 and are shown in Table 2.

TABLE 2

Physical Properties-ASTM D-412

| | |
|---|---|
| Thickness | 4.5 mils |
| Tensile Strength | 2200 psi |
| Elongation | >800% |
| 500% modulus | 350 psi |

The puncture resistances of the gloves from Example 1, of a conventional natural rubber latex examination glove, and of a conventional natural rubber latex surgical glove were measured according to ASTM D-120 and the results are shown in Table 3. Table 3 illustrates the superior puncture resistance of the gloves made according to Example 1.

TABLE 3

PUNCTURE RESISTANCE-ASTM D-120

| Glove | lbs. | gauge | lbs./inch |
|---|---|---|---|
| NR examination | 1.9 | 6.7 | 281 |
| NR surgical | 2.9 | 7.5 | 396 |
| Example 1 | 3.9 | 4.7 | 842 |

The resilience of the gloves made according to Example 1 and a conventional natural rubber latex glove was tested as follows. A sample was cut from each glove and stretched 100% of its length to determine the initial 100% modulus according to ASTM D-412. The amount of stress required to maintain this 100% stretch was then recorded every minute for 30 minutes. The resulting data is shown in FIGS. 1 and 2. FIG. 1 is a plot of percent of initial stress versus time for the sample from the Example 1 glove and the sample from the conventional natural rubber glove. FIG. 2 is a plot of stress in psi versus time for the same samples. As can be seen from FIGS. 1 and 2, the stress required to maintain the 100% stretch of the Example 1 glove sample was substantially zero within six minutes after the initial stretch, while the stress required to maintain the 100% stretch of the conventional glove sample dropped to only about 80% of the initial stress over the 30 minute period.

The foregoing description relates only to preferred embodiments of the present invention, and numerous changes and modifications may be made therein without departing from the spirit and scope of the invention as defined in the following claims.

What is claimed is:

1. A *closely fitting* glove comprising a layer of elastomeric material (*a*) *comprising nitrile butadiene rubber*, (*b*) having an initial configuration adapted to receive *and fit closely about* a hand, and (*c*) characterized by (*i*) being substantially impermeable to water vapor and liquid water, (*ii*) having a tensile strength of at least about 1500 psi as measured according to ASTM D-412 on a sample of the elastomeric material having a thickness from about 4.0 to about 4.5 mils, and (*iii*) having a *thickness and* elastic properties such that *the glove is capable of being stretched to fit closely about the hand and* when stretched from the initial configuration to fit *closely* about the hand, the elastomeric material conforms to the configuration of the hand, initially exerting [a predetermined] *an initial* pressure on the hand and thereafter *still fitting closely about the hand, but* relaxing, *within about 6 minutes after the glove is stretched to fit about said hand,* to exert on the hand a reduced pressure which is [substantially] less than about [80%] *50%* of the [predetermined] *initial* pressure.

2. A glove as in claim 1, wherein the layer of elastomeric material *further* comprises [nitrile butadiene rubber and] a metallic compound which is substantially insoluble in water and is present in an amount effective to impart said tensile strength without significantly stiffening the elastomeric material and altering said elastic properties.

3. A glove as in claim 2 wherein the metallic compound comprises a metal selected from the group consisting of lead, magnesium and zinc.

4. A glove as in claim 2 wherein the metallic compound comprises metallic oxide.

5. A glove as in claim 4 wherein the metallic oxide is selected from the group consisting of lead oxide, magnesium oxide and zinc oxide.

6. A glove as in claim 2 wherein the metallic compound comprises zinc oxide present in an amount from about 0.1 to about 0.5 parts per 100 parts nitrile butadiene rubber.

7. A glove as in claim 1, wherein the *nitrile butadiene rubber comprises carboxylated nitrile butadiene rubber and the* layer of elastomeric material *further* comprises [carboxylated nitrile butadiene rubber and] a metallic compound which is substantially insoluble in water and is present in an amount effective to impart said tensile strength without significantly stiffening said elastomeric material and said elastic properties.

8. A glove as in claim 7 wherein the metallic compound comprises a metal selected from the group consisting of lead, magnesium and zinc.

9. A glove as in claim 7 wherein the metallic compound comprises metallic oxide.

10. A glove as in claim 9 wherein the metallic oxide is selected from the group consisting of lead oxide, magnesium oxide and zinc oxide.

11. A glove as in claim 7 wherein the metallic compound comprises zinc oxide present in an amount from about 0.1 to about 0.5 parts per 100 parts nitrile butadiene rubber.

[12. A glove as in claim 1, wherein the layer of elastomeric material is further characterized by having elastic properties such that said reduced pressure is reached within 6 minutes after the glove is stretched to fit about said hand.]

[13. A glove as in claim 1, further characterized by having elastomeric properties such that the reduced pressure is less than about 50% of said predetermined pressure.]

14. A glove as in claim [13] *1* further characterized by having elastic properties such that said reduced pressure is reached within about one minute after the glove is stretched to fit about said hand.

15. A glove as in claim 1, wherein the layer of elastomeric material is further characterized by having elastic properties such that said reduced pressure is less than about [90%] *10%* of said [predetermined] *initial* pressure.

[16. A glove as in claim 15, wherein the layer of elastomeric material is further characterized by having elastic properties such that said reduced pressure is reached within about 6 minutes after the material is stretched to fit about said hand.]

*17. A glove as in claim 1, wherein the layer of elastomeric material has a thickness up to about 4.5 mils.*

*18. A glove as in claim 1, wherein the layer of elastomeric material has a thickness from about 4 to about 4.5 mils.*

*19. A glove as in claim 1, wherein the layer of elastomeric material is further characterized by having a puncture resistance of greater than about 800 lbs/in.*

*20. A glove as in claim 1, wherein the layer of elastomeric material is further characterized by having an elongation of greater than about 800%.*

*21. A glove as in claim 1, wherein the layer of elastomeric material is further characterized by having a 500% modulus up to about 350 psi.*

*22. A glove as in claim 1, wherein the layer of elastomeric material is further characterized by having a 500% modulus in the range from about 250 to about 350 psi.*

*23. A glove as in claim 1, wherein the layer of elastomeric material is further characterized by having elastomeric properties such that said reduced pressure is about zero.*

*24. A glove as in claim 1, wherein the nitrile butadiene rubber comprises carboxylated nitrile butadiene rubber.*

* * * * *